United States Patent [19]
Johnson

[11] Patent Number: 5,800,779
[45] Date of Patent: Sep. 1, 1998

[54] DIAGNOSTIC SAMPLING DEVICE AND SYSTEM FOR ANALYZING BODY FLUIDS

[76] Inventor: Theodore D. Johnson, 2219 Glenmoor Rd., South, Clearwater, Fla. 34624

[21] Appl. No.: 559,858

[22] Filed: Nov. 20, 1995

[51] Int. Cl.⁶ .................................................. G01N 33/16
[52] U.S. Cl. .................. 422/58; 422/101; 422/102; 436/163; 436/180; 128/760; 128/771
[58] Field of Search .................. 422/55, 58, 61, 422/100, 101, 102, 104; 436/63, 68, 164, 165, 169, 174, 175, 177, 178, 163, 180; 128/760, 771

[56] References Cited

U.S. PATENT DOCUMENTS

| | | | |
|---|---|---|---|
| 2,941,869 | 6/1960 | Brown et al. | 422/58 |
| 3,982,538 | 9/1976 | Sharpe . | |
| 4,160,008 | 7/1979 | Fenocketti et al. | 422/56 |
| 4,180,383 | 12/1979 | Johnson | 422/69 |
| 4,323,536 | 4/1982 | Columbus | 422/56 |
| 4,409,182 | 10/1983 | Macklem | 422/61 |
| 4,769,216 | 9/1988 | Chandler et al. | 422/58 |
| 4,813,931 | 3/1989 | Hauze . | |
| 4,865,813 | 9/1989 | Leon | 422/101 |
| 4,874,691 | 10/1989 | Chandler | 435/7 |
| 4,904,605 | 2/1990 | O'Brien et al. | 436/169 |
| 4,917,671 | 4/1990 | Chang . | |
| 4,950,247 | 8/1990 | Rosenblatt . | |
| 4,952,516 | 8/1990 | Matkovich | 436/170 |
| 4,960,565 | 10/1990 | Shurben | 422/61 |
| 5,000,919 | 3/1991 | Heckmann | 422/58 |
| 5,100,620 | 3/1992 | Brenneman | 422/58 |
| 5,166,075 | 11/1992 | Fehder | 436/133 |
| 5,238,655 | 8/1993 | Laible et al. . | |
| 5,366,902 | 11/1994 | Cox et al. | 436/165 |
| 5,429,803 | 7/1995 | Guirguis | 422/58 |
| 5,429,804 | 7/1995 | Sayles | 422/58 |

OTHER PUBLICATIONS

Metheny, Norma A. et al, "pH Testing of Feeding–Tube Aspirates to Determine Placement," *Nutrition in Clinical Practice*, 9: 185–90 (Oct. 1994).

*Primary Examiner*—Long V. Le

[57] ABSTRACT

A diagnostic sampling device and system for analyzing body fluids includes a transparent housing defining a test chamber therein in communication with a fluid inlet and a gas outlet, a test strip disposed in the test chamber and having an indicating portion reactive to a condition of the body fluids, and a ruler positionable outside the housing adjacent the test chamber for comparison with indicating portions of the test strip. A plug disposed in the gas outlet of the housing permits gas flow while preventing passage of body fluids, and is preferably formed of a porous material having a capacity to seal the gas outlet when contacted by body fluids. An absorbent filter is also disposed in the housing between the fluid inlet and the test chamber. The fluid inlet can be configured to couple with the proximal end of an enteral feeding tube, in which case the gas outlet is preferably configured to couple with a syringe so that the housing can be filled in-line with aspirated body fluids drawn from the enteral feeding tube by creating suction with the syringe. Alternatively, the fluid inlet can be configured to couple with a syringe such that body fluids can be aspirated from the enteral feeding tube directly using the syringe and expelled into the housing off-line via the fluid inlet.

19 Claims, 6 Drawing Sheets

DIAGNOSTIC SAMPLING DEVICE AND SYSTEM FOR ANALYZING BODY FLUIDS

A portion of the disclosure of this patent document contains material which is subject to copyright protection. The copyright owner has no objection to the facsimile reproduction by anyone of the patent disclosure, as it appears in the Patent and Trademark Office patent files or records, but otherwise reserves all copyright rights whatsoever.

BACKGROUND OF THE INVENTION

1. Field of the Invention

The present invention relates to a diagnostic sampling device and system for analyzing body fluids and, more particularly, to a diagnostic sampling device and system for testing the pH of feeding tube aspirates.

2. Discussion of the Prior Art

Enteral feeding tubes inserted through the nasal cavity and guided via the nasopharynx and esophagus into either the stomach or small intestine are used to administer nutrients and medication to patients unable to be fed by mouth. Such tubes are typically about 20 to 55 inches long with a perforated distal end or tip for positioning within the body and one or more ports located outside the body at a proximal end of the tube for administering nutrients and medication and aspirating body fluids.

To insure proper placement of an enteral feeding tube, medical personnel must be able to determine the location of the tip of the tube in the body. For example, while some patients may safely receive feedings in the stomach, others may need feedings in the distal duodenum or proximal jejunum; and, accordingly, medical personnel must be able to differentiate between gastric and intestinal feeding tube placement. Medical personnel must also be able to differentiate between gastric and respiratory placement of the feeding tube, since failure to detect respiratory placement of the tube prior to administering nutrients can be fatal.

Feeding tube placement within the body is often confirmed using radiologic or x-ray techniques requiring radiopaque materials such as barium sulfate to be used in forming the enteral feeding tube. Markings on the tube can also be used as a reference when determining the length of the tube inserted. However, when used alone, tube markings provide only a rough approximation of the actual location of the tip of the tube and, since feeding tube placement is typically confirmed at the time of initial insertion and before each intermittent feeding, the practice of using x-rays to locate the tip of the tube can increase the risk of harm to the patient from repeated exposure to x-rays as well as the overall cost of treating the patient.

Other methods of confirming tube position within the body, such as the auscultatory method, are largely ineffective in differentiating between gastric and intestinal location and in ruling out accidental tube placement in the lung.

Recent studies suggest that pH testing of aspirates from enteral feeding tubes can reduce the need for x-ray confirmation of tube placement. See, e.g., Metheny et al, "pH Testing of Feeding-Tube Aspirates to Determine Placement," *Nutrition in Clinical Practice*, 9:185–190 (October 1994). In addition, intermittent pH testing of feeding tube aspirates can assist in monitoring the effectiveness of certain therapies, thereby providing useful information that can be used by medical personnel to adjust the therapies accordingly.

Currently, pH testing of feeding tube aspirates is accomplished using a syringe to draw fluid directly from the open proximal end of the enteral feeding tube, after which the fluid is deposited onto a chemical strip, such as litmus, for analysis. A disadvantage of this method is that the body fluids are tested in the open and not contained, thereby increasing the risk of contaminating the sample and exposing medical personnel to infectious diseases.

Some of these problems can be avoided by testing the pH of body fluids in vivo using an enteral feeding tube with an integral pH electrode at the tip of the tube and a separate readout module or monitor. A disadvantage of such enteral feeding tubes, however, is that they do not provide direct visual observation of the body fluids being tested so that it is difficult to differentiate between mucosal and pooled gastric-intestinal body fluids. Also, the cost of such enteral feeding tubes and monitors is high when compared to standard enteral feeding tubes, and the tubes must continually be calibrated with the monitors requiring greater technical skill and increasing the likelihood of error.

SUMMARY OF THE INVENTION

Accordingly, it is a primary object of the present invention to overcome the disadvantages of the prior art and to provide a diagnostic sampling device and system for analyzing body fluids.

It is another object of the present invention to protect medical personnel from contacting sampled body fluids and to prevent contamination of the body fluids when depositing the body fluids onto test strips outside the body.

Yet another object of the present invention is to facilitate pH testing of feeding tube aspirates by collecting the aspirates in a test chamber of a diagnostic sampling device and observing the reaction of a test strip disposed within the chamber of the device.

A further object of the present invention is to more easily determine the pH of feeding tube aspirates by comparing one or more colors on a test strip exposed to feeding tube aspirates in a test chamber of a diagnostic sampling device with reference colors positioned outside the device on a pH ruler.

Some of the advantages of the present invention over the prior art are that the diagnostic sampling device can be used with conventional enteral feeding tubes and syringes, that the diagnostic sampling device is essentially sealed during testing to prevent leakage of body fluids from the device, that no special training or expertise is required in order to use the diagnostic sampling device, that the diagnostic sampling device does not require calibration prior to use, that the diagnostic sampling device can be inexpensively manufactured to facilitate disposal after use, and that the diagnostic sampling device can be used with auscultation and other clinical indicators to determine feeding tube placement.

The present invention is generally characterized in a diagnostic sampling device for analyzing body fluids including a housing defining a test chamber therein in communication with a fluid inlet and a gas outlet, and a test strip disposed in the test chamber and having an indicating portion visible through the test chamber and reactive to a characteristic of the body fluids. A plug disposed in the gas outlet of the housing permits gas flow while preventing passage of body fluids, and is preferably formed of a porous material having a capacity to seal the gas outlet when contacted by body fluids. The fluid inlet can be configured to couple with the proximal end of an enteral feeding tube, in which case the gas outlet is preferably configured to couple with a syringe so that the housing can be filled in-line with aspirated body fluids drawn from the enteral feeding tube by creating suction with the syringe. Alternatively, the fluid inlet can be configured to couple with a syringe such that body fluids can be aspirated from the enteral feeding tube directly using the syringe and expelled into the housing off-line via the fluid inlet.

Another aspect of the present invention is generally characterized in a diagnostic system including a sampling device as described above and a ruler with a plurality of reference patterns formed thereon, the ruler being positionable outside the sampling device adjacent the test chamber to facilitate comparison of the reference patterns with indicating portions of the test strip disposed in the test chamber.

A further aspect of the present invention is generally characterized in a method of analyzing body fluids including the steps of collecting body fluids within an enclosed test chamber having a test strip disposed therein, the test strip including at least one indicating portion reactive to a characteristic of the body fluids, and determining a characteristic of the body fluids by observing the reaction of the indicating portion through the test chamber. In one embodiment, the test chamber communicates with a fluid inlet and a gas outlet, and the body fluids are collected by connecting the fluid inlet with the proximal end of an enteral feeding tube, connecting a syringe with the gas outlet and drawing vacuum via the gas outlet using the syringe. In another embodiment, the body fluids are drawn into a syringe from an enteral feeding tube and expelled into the housing from the syringe via the fluid inlet.

Yet another aspect of the present invention is generally characterized in a method of testing the pH of feeding tube aspirates including the steps of aspirating fluids from the body via a feeding tube, collecting the body fluids in an enclosed test chamber having a test strip disposed therein, the test strip including at least one indicating portion reactive to pH, positioning a ruler outside the test chamber adjacent the test strip, and comparing a plurality of reference patterns formed on the ruler with the indicating portion on the test strip to determine the pH of the body fluids. In a preferred embodiment, the comparing step includes positioning a first row of reference patterns alongside the indicating portion of the test strip and moving the ruler lengthwise to align individual reference patterns with the indicating portion, after which the ruler can be inverted and/or flipped over to position additional rows of reference patterns alongside the indicating portion of the test strip.

Other objects and advantages of the present invention will become apparent from the following description of the preferred embodiments taken in conjunction with the accompanying drawings, wherein like parts in each of the several figures are identified by the same reference characters.

DESCRIPTION OF THE PREFERRED EMBODIMENTS

A diagnostic sampling device or sampler assembly 20 according to the present invention, as shown in FIGS. 1–5, includes an optically transparent housing 22 with a test chamber 24 defined therein in communication with a fluid inlet 26 and a gas outlet 28. A test strip 30 having indicating portions 32a, 32b and 32c reactive to pH is received within the test chamber and is visible through the transparent housing. Also received within the housing are an absorbent filter 36 disposed between the fluid inlet and the test chamber and a porous plug 38 disposed in the gas outlet.

Housing 22 includes an upper housing portion 40 coupled with a lower housing portion 42. Upper housing portion 40 includes a generally circular base 44 mounting the test chamber 24, the gas outlet 28 and a pair of alignment pegs 34a and 34b. A cylindrical extension 46 depends downwardly, looking at FIG. 3, from a peripheral edge of the base to a horizontal ledge or shoulder 48 extending perpendicularly from the bottom of the cylindrical extension in a radial direction, the shoulder 48 terminating radially at a cylindrical lip 50 depending downwardly from a peripheral edge of the shoulder. Lower housing portion 42 includes a generally circular base 52 with a central hole 54 formed therethrough and ribs 56 extending radially outward from angularly spaced locations around the hole to a ridge 58 radially spaced inwardly of the peripheral edge of the base, the ridge 58 including tapered sides that combine to form an edge spaced radially inward of the lip 50 in alignment with the horizontal shoulder 48 of the upper housing when the upper and lower housings are assembled as shown in FIG. 3.

Figure 3:
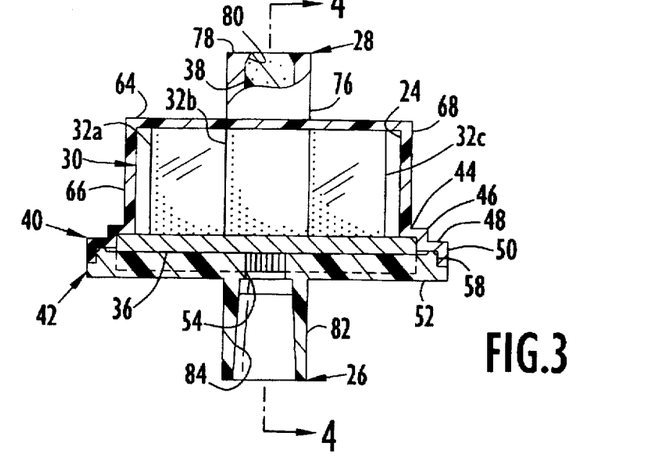
FIG. 3 is a front view, partly in section, of the diagnostic sampling device of FIG. 1.
Figure 4:
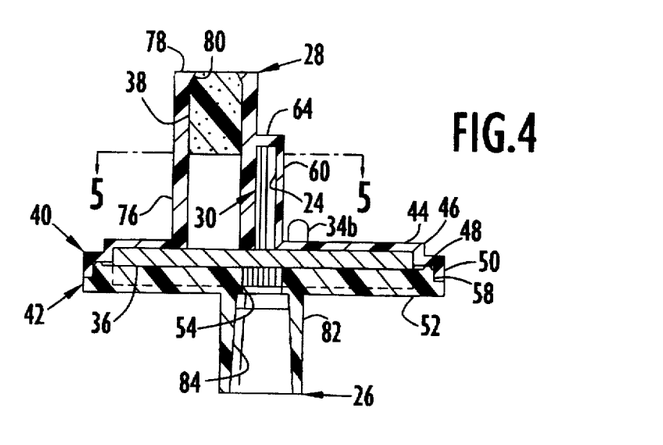
FIG. 4 is a sectional side view of the diagnostic sampling device taken through line 4—4 in FIG. 3.
Figure 5:
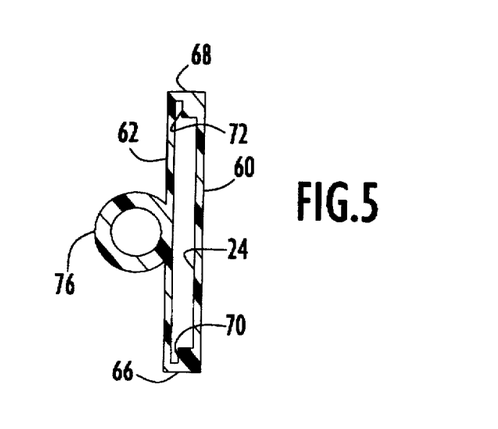
FIG. 5 is a sectional top view of the diagnostic sampling device taken through line 5—5 in FIG. 4.

Test chamber 24 extends upwardly, looking at FIG. 3, from a rectangular opening in the circular base 44 and is generally rectangular in shape with front and back walls 60 and 62 oriented substantially perpendicular to the base, a top wall 64 extending perpendicularly between upper longitudinal edges of the front and back walls, and laterally opposed side walls 66 and 68 extending perpendicularly between lateral edges of the front and back walls from the base 44 to the top wall 64. A pair of slots or grooves 70 and 72 are formed on opposite sides of the test chamber in opposed side walls 66 and 68 adjacent back wall 62 to define tracks or guides to assist in locating the test strip within the test chamber.

Test strip 30 is received within the test chamber between grooves 70 and 72 and is formed of a generally rectangular band or strip 74 having one or more reactive indicating portions 32a, 32b and 32c formed of litmus and/or other materials reactive to a physical or chemical condition or characteristic of a fluid.

Gas outlet 28 includes a hollow cylinder or tube 76 located behind the test chamber and extending upward, looking at FIG. 3, from a circular opening in the base to a terminal end 78 vertically spaced above the top wall of the test chamber. An inwardly extending radial flange 80 is formed at terminal end 76 with plug 38 being disposed in the gas outlet tube 76 adjacent the flange and having a generally cylindrical shape with a diameter to frictionally fit within the tube. The plug is preferably formed of a porous material such as, for example, a self-sealing porous polyethylene which, when wetted, creates a seal preventing passage of body fluids and air through the gas outlet.

Fluid inlet 26 includes a hollow cylinder or tube 82 extending downwardly from lower housing portion 42, looking at FIG. 3. The tube is configured as a female luer fitting with a tapered bore 84 having a configuration to receive the dispensing tip of a syringe, the bore being aligned with the central hole 54 in the circular base of the lower housing portion. Absorbent filter 36 is disposed within the housing between the fluid inlet 26 and the test chamber 24 to absorb and hold body fluids entering the housing and to remove particulates from the body fluids. The filter is shown as a disk but can have any shape to fit between the fluid inlet and the test chamber and can be formed of any absorbent filter material. Preferably, the filter is formed of cotton prefilter material and arranged such that a bottom surface of the filter rests upon the ribs of the lower housing portion 42 and a top surface of the filter abuts the circular base of the upper housing portion 40.

Figure 6:
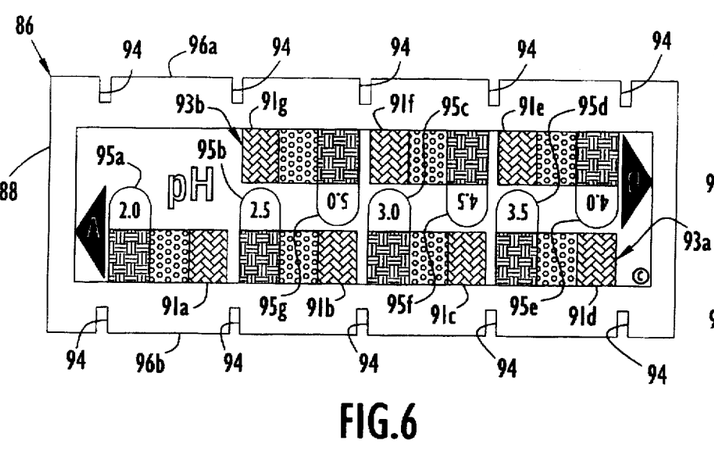
FIG. 6 is a front view of a pH ruler for use with the diagnostic sampling device of the present invention.
Figure 7:
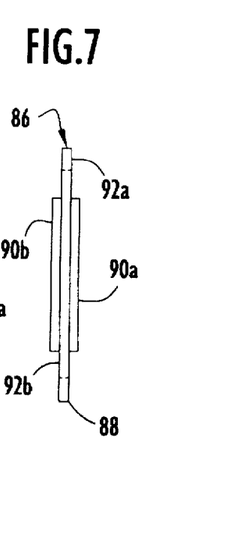
FIG. 7 is a side view of the pH ruler shown in FIG. 6.
Figure 8:
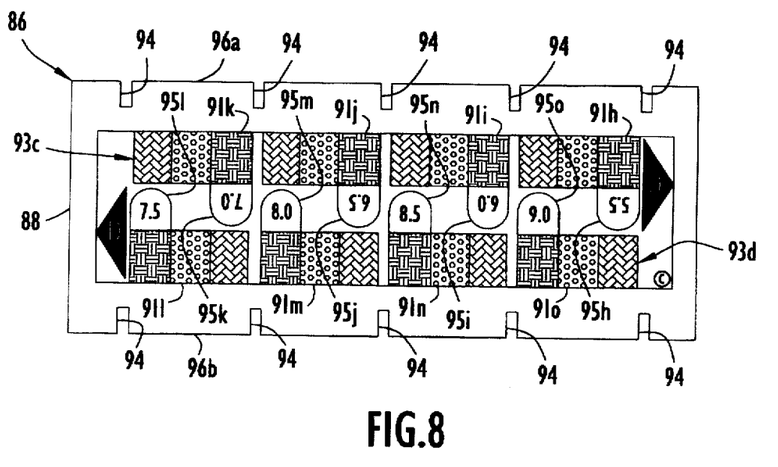
FIG. 8 is a rear view of the pH ruler shown in FIG. 6.

A pH ruler 86, shown in FIGS. 6–8, is formed separately from the diagnostic sampling device 20 but is useable therewith as part of a diagnostic system according to the present invention. The pH ruler 86 is essentially a standard or key for determining pH from the reactive patterns formed by indicating portions 32a, 32b and 32c. The pH ruler 86 is formed of a generally rectangular card or plate 88 made of clear plastic or some other transparent material with printed portions 90a and 90b on front and back faces 92a and 92b, respectively, of the card. Printed portions 90a and 90b include reference patterns 91a–o corresponding to specific pH values arranged sequentially in parallel rows 93a–d on both sides of the ruler. Scale markings 95a–o are disposed alongside the reference patterns in the space between rows to identify the pH indicated by an adjacent reference pattern, individual rows 93a–d being labelled A, B, C and D, respectively, to designate the range of pH indicated by a particular row. For example, row A on the front face 92a of the ruler includes four reference patterns 91a–d each made up of three rectangular sections similar in size and shape to indicating portions 32a, 32b and 32c. Reference patterns 91a–d are arranged from left to right in order of increasing pH with the leftmost reference pattern 91a corresponding to a pH of about 2.0 and the rightmost reference pattern 91d corresponding to a pH of about 3.5. Markings 95a–d representing increments of 0.5 on the pH scale are placed above the first rectangular section of each pattern in row A. Row B is spaced above row A on the first side of the ruler with three reference patterns 91e, 91f and 91g arranged right to left in order of increasing pH, the rightmost reference pattern 91e corresponding to a pH of about 4.0 and the leftmost reference pattern 91g corresponding to a pH of about 5.0. Markings 95e–g, representing increments of 0.5 on the pH scale, are placed beneath the first rectangular section of each pattern in row B and are upside down or inverted, looking at FIG. 6. Rows C and D on the back side of the ruler include four reference patterns 91h–k and 91l–o, respectively, arranged in order of increasing pH. The reference patterns 91h–k of row C are arranged right to left, looking at FIG. 8, along an upper edge of the printed portion in order of increasing pH, the rightmost reference pattern 91h corresponding to a pH of about 5.5 and the leftmost reference pattern 91k corresponding to a pH of about 7.0. Markings 95h–k, representing increments of 0.5 on the pH scale, are placed beneath the first rectangular section of each reference pattern in row C and are upside down or inverted, looking at FIG. 8. The reference patterns 91l–o of row D are arranged left to right beneath row C in order of increasing pH, the leftmost reference pattern 91l corresponding to a pH of about 7.5 and the rightmost reference pattern 91o corresponding to a pH of about 9.0, markings 95l–o being placed above the first rectangular section of each reference pattern in row D and representing increments of 0.5 on the pH scale. Rectangular notches 94 are formed along opposite, longitudinal edges 96a and 96b of the ruler in longitudinal alignment with opposite ends of each row and spaces between adjacent reference patterns in a row such that, when the ruler is placed directly in front of the test chamber, a pair of notches on the lowermost edge of the ruler beneath one of the reference patterns will receive alignment pegs 34a and 34b formed on the circular base of the upper housing portion 40 in front of test chamber 24 thereby accurately positioning one of the reference patterns above indicating portions 32a, 32b and 32c of the test strip for easy comparison.

Figure 1:
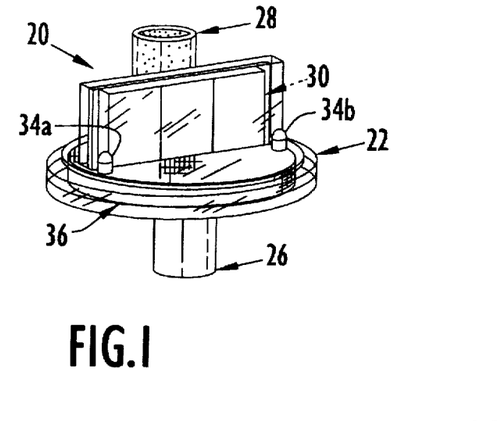
FIG. 1 is a perspective view of a diagnostic sampling device according to the present invention.
Figure 2:
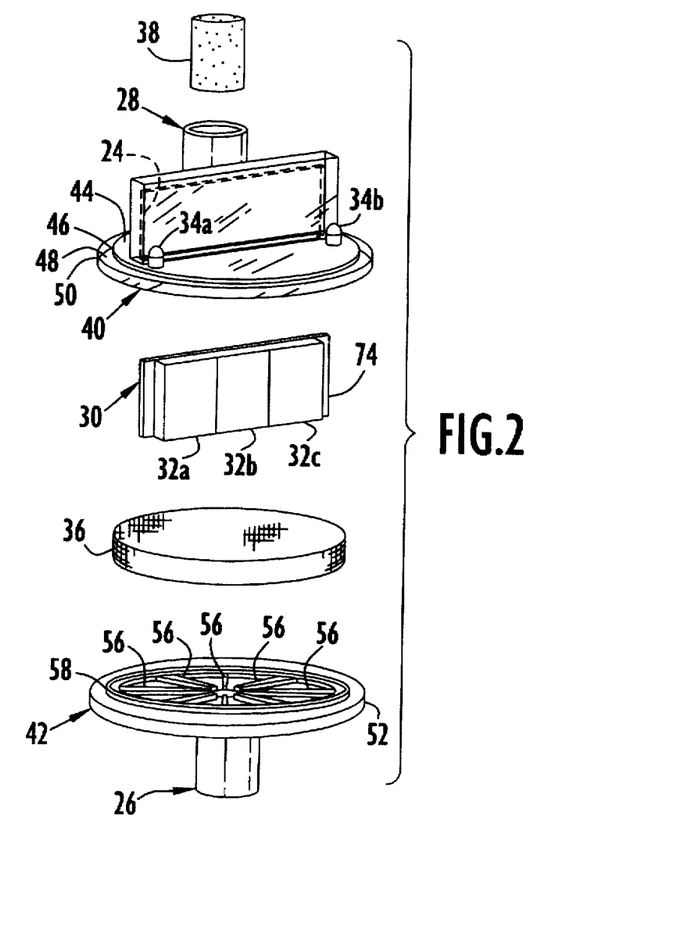
FIG. 2 is an exploded view, in perspective, of the diagnostic sampling device of FIG. 1.

The diagnostic sampling device 20 can be assembled by inserting a desired test strip 30 into the test chamber 24 of the upper housing portion 40 with opposite ends of the strip aligned with slots 70 and 72 formed in sidewalls 66 and 68. The strip 30 is advanced along slots 70 and 72 until it abuts the top wall 64 of the chamber such that indicating portions 32a, 32b and 32c are visible through the transparent walls of the chamber. Plug 38 is positioned in the gas outlet 28 by inserting the plug in the circular opening in the base 44 of the upper housing 40 and pushing the plug upward in the gas outlet tube 76 until the plug abuts radial flange 80 at the terminal end of the tube. Absorbent filter 36 can then be placed against the circular base 44 of the upper housing portion within the cylindrical recess formed by extension 46 and in contact with a lower edge of test strip 30. The filter is held in place by inserting the ridge 58 of the lower housing portion 42 telescopically within the rim 50 of the upper housing portion 40 to couple with and frictionally engage the upper housing portion. The assembly is preferably sealed by ultrasonically welding together the upper and lower housing portions so that, when the fluid inlet and gas outlet are sealed during use, the test chamber is completely enclosed and body fluids cannot escape the housing.

In a preferred embodiment, the housing is formed of a transparent plastic material such as styrene acrylonitrile; however, any medically acceptable plastic or metal material can be used so long as the portion of the housing receiving the test strip is transparent or is otherwise able to accommodate observation of the test strip. The test strip can be formed of litmus or some other material reactive to a physical or chemical condition of a fluid and is preferably rectangular in shape with a length of about 0.815 inches and a height of about 0.315 inches. Indicating portions of the test strip are also rectangular and have a width of about 0.233 inches and a height equal to that of the strip. It is also preferred that the ruler be formed of a transparent plastic with a thickness of about 0.02 inches. The printed portions of the ruler preferably include reference patterns made up of three rectangular sections, each section having a width of about 0.2383 inches, a height of about 0.30 inches and a thickness of about 0.006 inches such that, with printed portions on both sides of the ruler, the overall thickness of the ruler will preferably be about 0.032 inches. Scale markings 95a–o are arranged between adjacent rows and are each preferably printed on an arch-like background. Row labels A, B, C and D are preferably located to the left of each row when viewed in an upright position and are printed on a dark triangular background pointing toward a lateral edge of the ruler.

Figure 9:
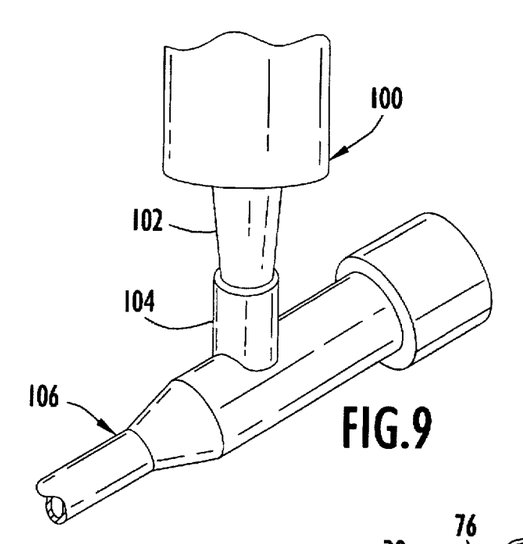
FIGS. 9–12 are perspective views illustrating use of the diagnostic sampling device of FIG. 1.
Figure 10:
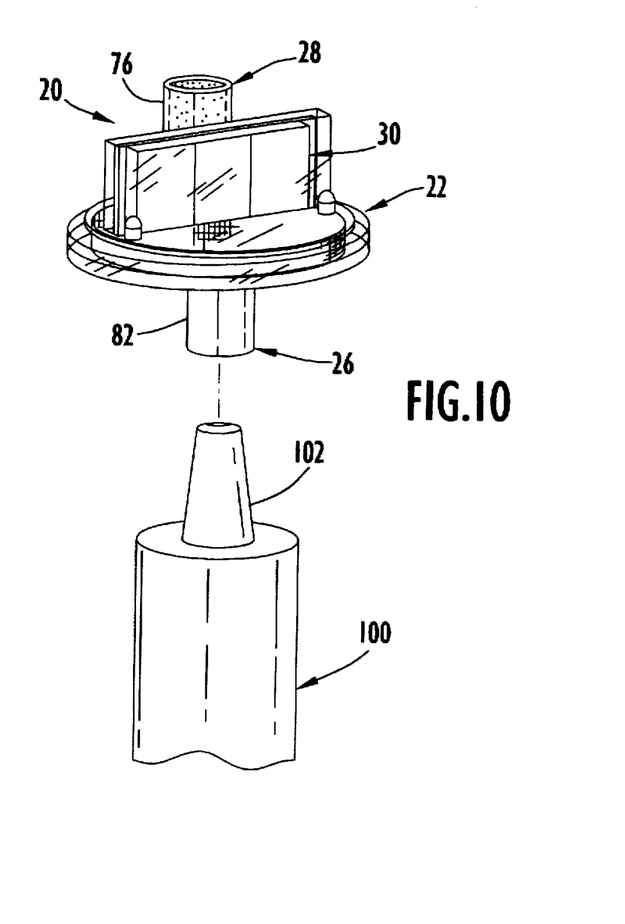
Figure 11:
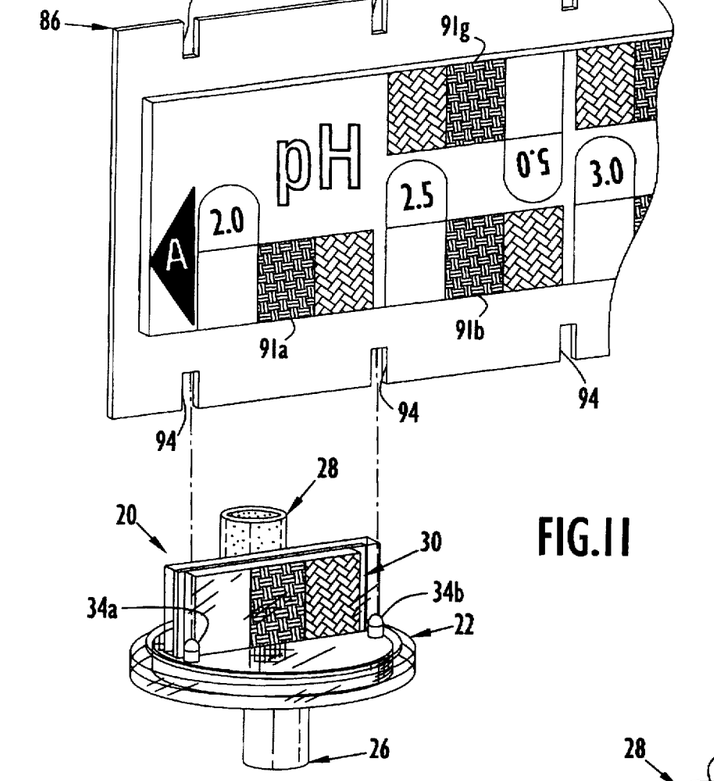

Use of the diagnostic sampling device 20 for pH testing body fluids, such as feeding tube aspirates, involves collecting the fluids from the body and introducing the collected fluids into the test chamber to interact with the test strip disposed therein. An "off-line" method of analyzing feeding tube aspirates is shown in FIGS. 9–12 wherein a conventional syringe 100 with a tapered dispensing tip 102 is inserted into an access port 104 at the proximal end of a standard enteral feeding tube 106 as shown in FIG. 9 and aspirates are drawn into the syringe via the enteral feeding tube in the conventional manner. When a sufficient quantity of feeding tube aspirates are collected, e.g., enough to fill the housing, syringe 100 is withdrawn from the feeding tube and the tip of the syringe inserted into the fluid inlet tube 82 of the diagnostic sampling device 20 as shown in FIG. 10. With the tapered bore of the fluid inlet tube 82 sealed by the tip of the syringe 100 and the gas outlet tube 76 in an upright vertical position as shown, the contents of the syringe 100 are injected into the diagnostic sampling device 20. The feeding tube aspirates travel upward through the fluid inlet tube 82 and are delivered via the central hole 54 into the space between the absorbent filter 36 and lower housing base 52. The increase in flow resistance caused by absorbent filter 36 causes some of the feeding tube aspirates to spread radially outward from central hole 54 along ribs 56 until forced upward through the absorbent filter by absorption and/or incoming fluid. In the event the test chamber is not completely filled with feeding tube aspirates, the absorbent filter will retain some of the feeding tube aspirates so that they can be drawn upward onto the test strip 30 by capillary action. As the feeding tube aspirates enter and fill the diagnostic sampling device, air already present within the device is forced upward, looking at FIG. 10, through gas outlet tube 76 and plug 38 to be vented via the gas outlet 28. When the aspirates contact and wet the plug 38, the device is essentially full and the plug will expand to seal the gas outlet tube 76 thereby preventing body fluids from escaping the diagnostic sampling device. It will also be appreciated that any fluid pressure exerted on plug 38 by the feeding tube aspirates as the device is filled will cause the plug to be forced against radial flange 80 which will resist upward movement of the plug thereby preventing the plug from being forced out of the tube 76 as the device is filled. Aspirates within the test chamber 24 interact with reactive indicating portions 32a, 32b and 32c of the test strip 30 causing the indicating portions to change color and to form a combination or pattern of colors indicative of pH, which pattern can be visually observed through the transparent housing 22 and/or observed in other ways, such as by use of optical and electronic devices, for interpretation by medical personnel.

A preferred method of interpreting the resultant pH pattern involves comparing the resultant pattern with reference patterns 91a–o printed on the pH ruler 86. Comparisons are made by positioning the ruler 86 adjacent the test chamber 24 with a desired row or scale 93a–d disposed in a non-inverted, upright condition along a bottom edge of the ruler and notches 94 corresponding to a first of the reference patterns being aligned with pegs 34a and 34b in front of the test chamber. With pegs 34a and 34b received in notches 94, the test strip 30 is visible through a transparent portion of the ruler surrounding the printed portions such that a comparison can be made between the first reference pattern and the resultant test pattern formed by the test strip. The ruler 86 can be indexed or, in other words, removed from the pegs and translated lengthwise until a different pair of notches are aligned with the pegs, the indexing being continued until a match is found for the resultant pattern of colors. If, for example, a match is not found in row A after indexing the ruler 86, the ruler can be turned upside down or inverted and indexed in the same way to compare the reference patterns of row B with the resultant pattern. The ruler 86 can then be flipped about face to compare the reference patterns of rows C and D in the same manner.

Figure 12:
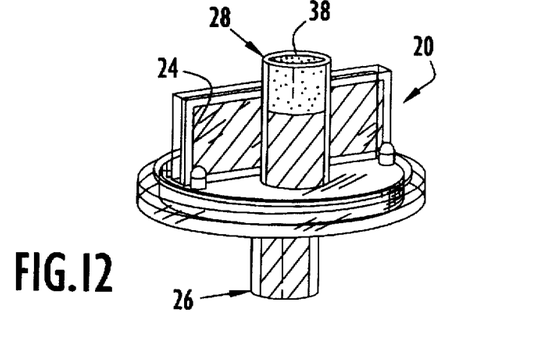

The diagnostic sampling device 20 can also be rotated about a vertical axis to be viewed from behind as shown in FIG. 12 to determine the color and appearance of the feeding tube aspirates, which information can be used along with pH values to confirm tube placement in the body. After use, the diagnostic sampling device and ruler are preferably disposed of to reduce the likelihood of medical personnel being exposed to body fluids.

Figure 13:
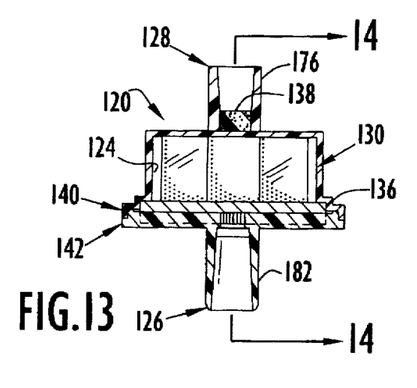
FIG. 13 is a front view, partly in section, illustrating a modification of the diagnostic sampling device according to the present invention.
Figure 14:
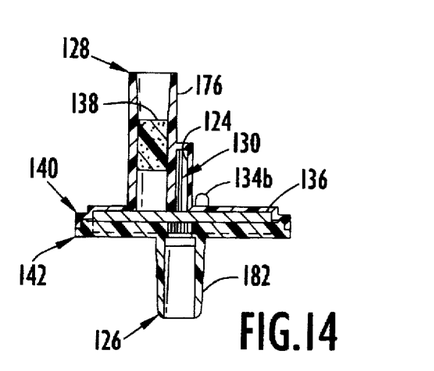
FIG. 14 is a sectional side view of the modified diagnostic sampling device taken through line 14—14 in FIG. 13.

The diagnostic sampling device of the present invention can be used "off-line" to test feeding tube aspirates from a syringe as described above or modified for "in-line" use wherein the device is coupled directly with an enteral feeding tube to test the feeding tube aspirates. For example, in FIGS. 13 and 14, a modified diagnostic sampling device 120 is shown having a fluid inlet 126 configured as a male luer fitting to couple with an access port of an enteral feeding tube and a gas outlet 128 configured as a female luer fitting to receive the dispensing tip of a syringe. Porous plug 138 is similar to the plug previously described above but is recessed within the gas outlet tube 176 to provide clearance for the tip of the syringe.

Figures 15, 16:
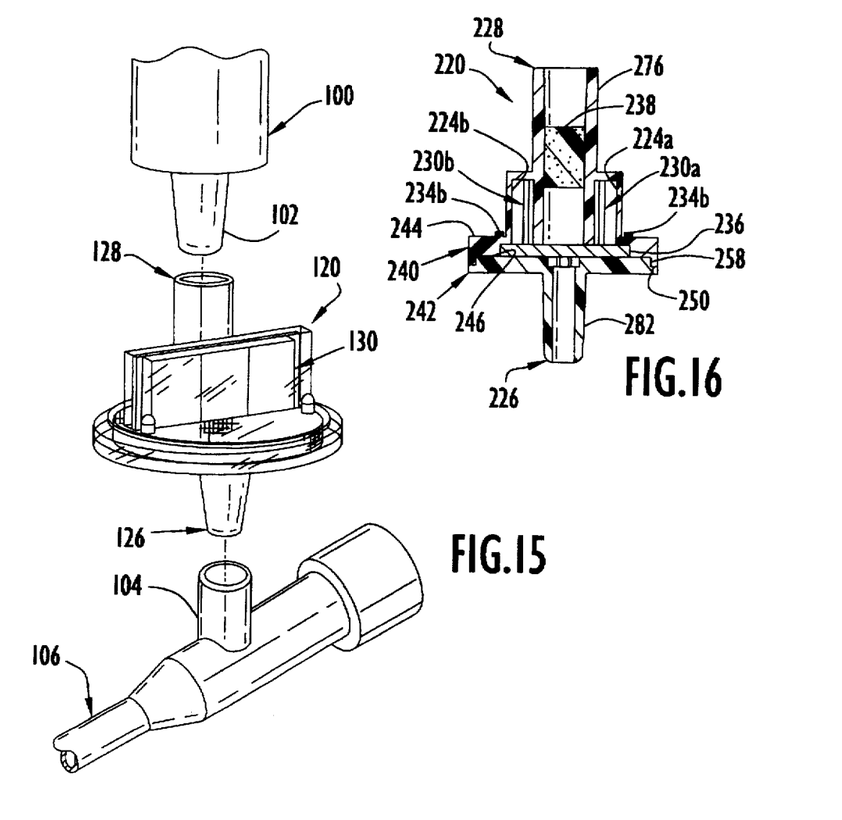
FIG. 15 is a perspective view illustrating use of the modified diagnostic sampling device of FIG. 13.
FIG. 16 is a sectional side view of another modification of the diagnostic sampling device according to the present invention.

In use, the modified diagnostic sampling device 120 is coupled with an enteral feeding tube 106 by inserting the fluid inlet tube 182 into the access port 104 at the proximal end of the feeding tube as shown in FIG. 15, or the sampling device can be formed integrally with the enteral feeding tube to be provided as a single unit. The dispensing tip 102 of a syringe 100 is placed in gas outlet tube 176 and used to draw air from the housing into the syringe thereby creating a sucking force at the fluid inlet. Feeding tube aspirates are drawn into the diagnostic sampling device 120 via the fluid inlet 126 and will fill the test chamber 124 as described above to interact with a test strip 130 so that medical personnel can analyze the aspirates in the manner described above.

A further modification of the diagnostic sampling device according to the present invention is shown in FIG. 16. The modified device 220 is similar to that shown in FIGS. 13 and 14 but with a pair of test chambers 224a and 224b formed on opposite sides of the gas outlet tube 276. The test chambers extend upwardly, looking at FIG. 16, from rectangular openings in the circular base 244 and are each generally rectangular in shape like the test chambers previously described above. Cylindrical base 244 is formed with a cylindrical recess 246 to receive the absorbent filter 236 and with a cylindrical rim 250 extending downwardly, looking at FIG. 14, from a peripheral edge of the circular base to define another cylindrical recess of larger diameter for receiving the ridge 258 of the lower housing portion.

The modified diagnostic sampling device 220 permits use of two test strips to analyze body fluids such that, for example, separate test strips reactive to different conditions or characteristics of the fluid can be used in respective test chambers to test for pH, trypsin, pepsin and bilirubin among other things.

From the above, it will be appreciated that the diagnostic sampling device and system of the present invention can be used to analyze any type of body fluid. By "analyze" is meant to determine, on the basis of a test, a physical or chemical characteristic or condition of the body fluid; and, accordingly, while the diagnostic sampling device and system have been described for use in testing the pH, or degree of acidity or alkalinity, of body fluids aspirated via an enteral feeding tube, it will be appreciated that other types of body fluids can be analyzed and that such analyses can involve other types of tests such as, for example, urine analysis.

The test strip can be any member, device or substance useful in analyzing body fluids including, but not limited to, the pH test strip described above. Any number of test strips can be received within a single test chamber or divided among multiple test chambers for testing one or more body fluid conditions. Any number of reactive indicating portions can be formed on a single test strip; and, when more than one indicating portion is formed on a test strip, the indicating portions can be located anywhere on the test strip and organized in any manner. For example, when multiple indicating portions are formed on a single test strip, they can be organized according to a specific body fluid condition tested such that, for example, one part of the strip will indicate pH while another part of the strip will indicate another characteristic of the fluid such as trypsin, pepsin and/or bilirubin. Moreover, the test strip can be modified to indicate pH values within a smaller or larger range than that described above and with any degree of accuracy desired.

The ruler can have any configuration to assist in interpreting the patterns or colors indicated by a test strip and will preferably include one or more reference patterns or colors corresponding to a specific value or range of values associated with a characteristic of the body fluids.

The test chamber can be of any shape or size to hold a test strip and body fluid including, but not limited to, rectangular, spherical or cylindrical configurations with grooves, clips or other retainers mounted therein for holding the test strip in place. In addition, the chamber can be formed with a door or flap to permit installation and/or removal of a test strip. When provided, such a door can be configured to be removable from the housing, can be hinged or can have any configuration allowing access to the chamber when open and sealing of the chamber when closed. Multiple test chambers of the same or different configuration can be provided when more than one type of test is to be performed.

The pegs and notches described above are merely exemplary of the types of mating structures that can be used to insure proper placement of the ruler against the housing and to facilitate indexed movement of the ruler. For example, the ruler could be formed with protrusions that fit within recesses formed in the housing and/or the ruler and housing could be provided with detents.

The fluid inlet and gas outlet can be of tubular configuration as shown or have any other configuration to permit passage of body fluids and gases, respectively, including configurations where the inlet and/or outlet are formed as openings in the housing without a tubular portion. The gas outlet is preferably disposed alongside the test chamber, with the fluid inlet being vertically aligned with the test chamber and offset from the gas outlet; however, the inlet and outlet can be vertically aligned at opposite ends of the test chamber, set at an angle relative to one another or disposed in any other manner depending on the desired flow pattern. In the case of the device being used "off-line," or separate from the enteral feeding tube, the fluid inlet is preferably formed with a female fitting to receive the dispensing tip of a syringe. In the case of the device being used "in-line," or connected with the enteral feeding tube, the fluid inlet is preferably formed with a male fitting to couple with the feeding tube while the gas outlet is preferably formed with a female fitting to receive the tip of a syringe. The fittings can include any type of known connector such as, for example, conventional luer-type fittings, friction fittings and threaded fittings with or without separate gaskets or seals.

The plug is preferably formed of a porous material which, when wetted, creates a seal with the gas outlet; however, any kind of material capable of preventing fluid flow through the gas outlet can be used including, but not limited to, known microporous hydrophobic materials.

The diagnostic sampling device is preferably provided in an assembled condition as shown but can also be provided as separate pieces for assembly by medical personnel. The device housing can be formed of multiple pieces or portions as shown or as an integral one-piece unit. The housing portions can be formed using conventional materials and methods such as injection molding and are preferably joined together and sealed by ultrasonic welding or any other suitable method including, but not limited to, friction fit, adhesive bonding, threaded engagement or any type of mechanical attachment. While the housing is preferably formed of an optically transparent material such as styrene acrylonitrile, it will be appreciated that any optically transparent, translucent or opaque material can be used to form major portions of the housing so long as certain portions of the housing remain transparent to permit observation of a test strip disposed within the housing.

Inasmuch as the present invention is subject to many variations, modifications and changes in detail, it is intended that all subject matter discussed above or shown in the accompanying drawings be interpreted as illustrative only and not be taken in a limiting sense.

What is claimed is:

1. A diagnostic sampling device for analyzing body fluids comprising a housing defining a test chamber therein in communication with a fluid inlet and a gas outlet; and a test strip disposed in said test chamber, said test strip being visible through said test chamber and having a plurality of indicating portions visibly reactive to pH of the body fluids;

said fluid inlet having a configuration to mate in sealing relation with a source of body fluids and said gas outlet having a configuration to permit gas flow while preventing passage of body fluids so that the diagnostic sampling device is essentially sealed during testing to prevent leakage of body fluids from the device.

2. A diagnostic sampling device as recited in claim 1 and further comprising a plug disposed in said gas outlet to permit gas flow while preventing passage of body fluids.

3. A diagnostic sampling device as recited in claim 2 wherein said plug is formed of a porous material having a capacity to seal said gas outlet when wetted by body fluids.

4. A diagnostic sampling device as recited in claim 1 and further comprising an absorbent filter disposed in said housing between said fluid inlet and said test chamber.

5. A diagnostic sampling device as recited in claim 1 wherein said indicating portions change color when contacted by body fluids, the combination of colors indicating the pH of the body fluids.

6. A diagnostic sampling device as recited in claim 1 wherein said gas outlet is configured to mate sealingly with the dispensing tip of a syringe so that, when a suction force is created with the syringe, body fluids will be drawn into said housing from the source of body fluids.

7. A diagnostic sampling device as recited in claim 6 wherein said fluid inlet is configured to mate sealingly with an access port at proximal end of an enternal feeding tube so that body fluids may be drawn directly from the body into said housing for analysis without exposure.

8. A diagnostic sampling device as recited in claim 1 wherein said fluid inlet is configured to mate sealingly with the dispensing tip a syringe.

9. A diagnostic system for analyzing body fluids comprising
- a sampling device including a housing defining a test chamber therein in communication with a fluid inlet and a gas outlet and a test strip disposed in said test chamber, said test strip being visible through said test chamber and having an indicating portion reactive to a characteristic of the body fluids, said fluid inlet having a configuration to mate in sealing relation with a source of body fluids and said gas outlet having a configuration to permit gas flow while preventing passage of body fluids so that the diagnostic sampling device is essentially sealed during testing to prevent leakage of body fluids from the device; and
- a ruler with at least one reference pattern formed thereon for comparison with the indicating portion of the test strip to determine the characteristic of body fluids contacting said test strip, said ruler being positionable outside said sampling device adjacent said test chamber to permit visual comparison of the indicating portion of the test strip and the reference pattern of the ruler without contaminating the body fluids or exposing medical personnel to infectious diseases.

10. A diagnostic system as recited in claim 9 wherein said ruler includes a plurality of reference patterns corresponding to a range of values used in describing a characteristic of the body fluids.

11. A diagnostic system as recited in claim 10 wherein said test strip includes a plurality of indicating portions and said reference patterns are about the same size and shape as said indicating portions.

12. A diagnostic system as recited in claim 9 wherein said housing and said ruler are configured to mate in at least one position placing a reference pattern alongside said indicating portion for comparison.

13. A diagnostic system as recited in claim 12 wherein said housing includes at least one peg and said ruler is notched to mate with said peg in at least one position.

14. A diagnostic system as recited in claim 10 wherein said indicating portion is reactive to pH and said reference patterns correspond to a range of pH values.

15. A diagnostic system for analyzing body fluids comprising a sampling device as recited in claim 1 and further comprising means for interpreting the reaction of the indicating portion of the test strip.

16. A diagnostic system as recited in claim 12 wherein at least a portion of said ruler is transparent so that, when said ruler is mated with said housing, said indicating portion of said test strip is visible through said transparent portion of said ruler for comparison with said reference pattern.

17. A diagnostic system as recited in claim 16 wherein said housing includes a base and said test chamber extends upwardly from said base to position said test strip such that, when said ruler is positioned against said base, said indicating portion of said test strip is visible through said transparent portion of said ruler.

18. A diagnostic sampling device for analyzing body fluids comprising
- a housing defining a test chamber therein in communication with a fluid inlet configured to mate sealingly with the dispensing tip of a syringe and a gas outlet;
- a plug disposed in said gas outlet and having a configuration to permit gases to vent while preventing passage of body fluids;
- said gas outlet including means engaging said plug to prevent expulsion of said plug as body fluids are injected into said fluid inlet from the syringe; and
- a test strip disposed in said test chamber, said test strip being visible through said test chamber and having an indicating portion visibly reactive to pH of the body fluids.

19. A diagnostic sampling device for analyzing feeding tube aspirates comprising
- a housing defining a test chamber therein in communication with a fluid inlet configured to mate sealingly with an access port at the proximal end of an enteral feeding tube and a gas outlet configured to mate sealingly with a dispensing tip of a syringe;
- a plug disposed in said gas outlet and having a configuration to permit gases to flow into the syringe from said housing so that a suction force can be created with the syringe to draw body fluids into said housing from the enteral feeding tube while preventing passage of the body fluids into the syringe through the plug; and
- a test strip disposed in said test chamber, said test strip being visible through said test chamber and having an indicating portion reactive to pH of the body fluids.

* * * * *